US009417196B2

(12) United States Patent
Kaercher

(10) Patent No.: US 9,417,196 B2
(45) Date of Patent: Aug. 16, 2016

(54) X-RAY DIFFRACTION BASED CRYSTAL CENTERING METHOD USING AN ACTIVE PIXEL ARRAY SENSOR IN ROLLING SHUTTER MODE

(71) Applicant: Bruker AXS Inc., Madison, WI (US)

(72) Inventor: Joerg Kaercher, Madison, WI (US)

(*) Notice: Subject to any disclaimer, the term of this patent is extended or adjusted under 35 U.S.C. 154(b) by 264 days.

(21) Appl. No.: 14/050,853

(22) Filed: Oct. 10, 2013

(65) Prior Publication Data

US 2015/0103980 A1  Apr. 16, 2015

(51) Int. Cl.
*G01N 23/20* (2006.01)
*G01N 23/207* (2006.01)

(52) U.S. Cl.
CPC ........ *G01N 23/207* (2013.01); *G01N 23/20016* (2013.01)

(58) Field of Classification Search
CPC ....... G01N 23/00; G01N 23/02; G01N 23/20; G01N 23/207; G01N 23/20008; G01N 23/20016; G01N 23/20025; G01N 23/20075; G01N 23/205; G01N 23/2055
See application file for complete search history.

(56) References Cited

U.S. PATENT DOCUMENTS

| | | | | |
|---|---|---|---|---|
| 5,741,707 A * | 4/1998 | Herron | ................... | G01N 23/20 436/161 |
| 6,782,076 B2 * | 8/2004 | Bowen | ................. | G01N 23/207 378/74 |
| 7,558,371 B2 * | 7/2009 | Park | ..................... | G01N 23/207 378/71 |
| 7,848,489 B1 * | 12/2010 | He | ....................... | G01N 23/207 378/71 |
| 8,903,043 B2 * | 12/2014 | Durst | ................... | G01N 23/207 378/70 |
| 9,103,769 B2 * | 8/2015 | Duden | ................. | G01N 23/203 |
| 2003/0108152 A1 * | 6/2003 | Bowen | ................ | G01N 23/207 378/74 |
| 2009/0103680 A1 * | 4/2009 | Park | ..................... | G01N 23/207 378/73 |
| 2009/0206368 A1 * | 8/2009 | Park | ..................... | G01N 23/207 257/194 |
| 2011/0174972 A1 * | 7/2011 | Duden | ................. | G01N 23/203 250/307 |
| 2013/0103339 A1 * | 4/2013 | Durst | ................... | G01N 23/207 702/104 |
| 2015/0046112 A1 * | 2/2015 | Durst | ................... | G01N 23/207 702/89 |
| 2015/0103980 A1 * | 4/2015 | Kaercher | ......... | G01N 23/20016 378/205 |

FOREIGN PATENT DOCUMENTS

EP        146397 A2    10/2004

OTHER PUBLICATIONS

Song et al., Diffraction-based automated crystal centering, Mar. 2007, Journal of Synchrotron Radiation, vol. 14, No. 2, p. 191-193, 195.*

(Continued)

*Primary Examiner* — Thomas R Artman
(74) *Attorney, Agent, or Firm* — Benoit & Coté, Inc.

(57) ABSTRACT

A method of centering a single crystal sample in the X-ray beam of a diffractometer uses detection of diffraction spots with an active pixel sensor operated in rolling shutter mode. A sample is mounted in the automated goniometer head of the diffractometer and an approximate center of the sample found through which three perpendicular sample axes pass. With a first sample axis perpendicular to a center axis of the X-ray beam, the sample is moved along the first axis from a first position outside of the beam, through the beam and then to a second position outside of the beam. The positions at which first the presence and then the absence of diffraction spots are detected are determined, and the steps repeated for each of the other two perpendicular directions. A precise center may then be found by determining the centroid of the six coordinates thereby obtained.

20 Claims, 8 Drawing Sheets

(56) References Cited

OTHER PUBLICATIONS

Seller et al., Pixellated Cd(Zn)Te high-energy X-ray instrument, Dec. 2011, Journal of Instrumentation, vol. 6, No. 12, p. 1, 2, 6.*
Karain, W. I., et al., Automated mounting, centering and screening of crystals for high-throughput protein crystallography, Acta Cryst. (2002), D58, 1519-1522.
Song, Jinhu, et al., Diffraction-based automated crystal centering, J. Synchrotron Rad. (2007), 14, 191-195.
Soltis, S. Michael, et al., New paradigm for macromolecular crystallography experiments at SSRL: automated crystal screening and remote data collection, Acta Cryst. (2008), D64, 1210-1221.
Aishima, Jun et al., High-speed crystal detection and characterization using a fast-readout detector, Acta Crystallographica Section D, Jul. 2010, p. 1032-1035.

* cited by examiner

X-RAY DIFFRACTION BASED CRYSTAL CENTERING METHOD USING AN ACTIVE PIXEL ARRAY SENSOR IN ROLLING SHUTTER MODE

BACKGROUND OF THE INVENTION

1. Field of the Invention

This invention relates generally to the field of X-ray diffraction and, more specifically, to the centering of a sample crystal for single-crystal diffraction analysis.

2. Description of the Related Art

Single-crystal X-ray diffraction (SC-XRD) is a method for determining the three-dimensional atomic structure of a crystalline compound. A single-crystal specimen of the compound is irradiated with monochromatic X-ray radiation from different directions, some of which is diffracted in specific patterns and detected by an active pixel sensor. The structural information of the specimen is determined from the geometry and relative intensities of these diffraction patterns. The intensities are integrated from the pixels in the active pixel array sensor images.

A typical laboratory system 100 for performing single-crystal diffraction experiments normally consists of five components as shown in FIG. 1. The components include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer 110 is used to establish and manipulate geometric relationships between the incident X-ray beam 108, the crystal sample 112 and the X-ray sensor 114. The incident X-ray beam 108 strikes the crystal sample 112 and produces scattered X-rays 116 which are recorded in the sensor 114. A sample alignment and monitor assembly comprises a sample illuminator 118 that illuminates the sample 112 and a sample monitor 120, typically a video camera, which generates a video image of the sample to assist users in positioning the sample in the instrument center and monitoring the sample state and position.

The goniometer 110 allows the crystal sample 112 to be rotated around several axes. Precise crystallography requires that the sample crystal 112 be aligned to the center of the goniometer 110 and maintained in that center when rotated around the goniometer rotational axes during data collection. During exposure, the sample (a single crystal of the compound of interest) is rotated in the X-ray beam 108 through a precise angular range with a precise angular velocity. The purpose of this rotation is to predictably bring Bragg reflections into constructive interference with the incident beam 108. During this time, called the charge integration time, the pixels of the sensor receive and integrate the X-ray signals.

The centering of the crystal in the goniometer prior to the start of the experiment may be done by a human operator by manually adjusting the translations of a goniometer head or by indicating the location of the specimen on a computer screen. Alternatively, the crystal centering can be done automatically using one of a number of conventional centering methods. These prior art methods fall, generally, into three different categories: mechanical methods; optical methods using computer vision algorithms; and X-ray diffraction based methods that use the intensity (or lack thereof) of the diffraction pattern produced by the specimen.

In the past, optical methods of centering appear to have been the most commonly used although, when automated, there are often problems with finding small crystals or those located in liquids. X-ray diffraction based methods of crystal centering have relied on the movement of the crystal relative to the X-ray beam while collecting diffraction images. Typically, the area to be scanned is broken down into points in a grid, and the X-ray beam is used to illuminate each point in the grid. The detected signal is then checked for the presence of diffraction spots for each of the illuminated grid points. In this way, the edges of the crystal can be found and, from that, the center of the crystal can be determined.

SUMMARY OF THE INVENTION

In accordance with the present invention, an X-ray diffraction based method for centering a crystal sample in the X-ray beam of an X-ray diffractometer uses a detector having active pixel array sensor operating in rolling shutter mode. The sample is mounted in the diffractometer and is then moved in and out of the X-ray beam while the detector is used to detect the presence and absence of diffraction spots. For example, as the sample is moved into the X-ray beam, diffraction spots will appear across the surface of the detector, and the diffraction data will be found in certain pixel rows of the sensor as those rows are read out. Similarly the disappearance of diffraction data in a row for which a diffraction spot was previously detected will indicate the movement of the sample out of the X-ray beam. Edge positions of the sample are thereby determined based on these appearances and disappearances of diffraction spots as the sample is moved, and these edge positions are then used to calculate a center of the sample.

In an exemplary embodiment, the sample is mounted in the diffractometer and an approximate center of the sample is determined through which three perpendicular sample axes pass. The sample is positioned outside of the X-ray beam such that a first of the sample axes is perpendicular to a center axis of the X-ray beam. The sample is then moved toward the X-ray beam along the first sample axis, while an active pixel array sensor operating in rolling shutter mode is used to detect any diffraction spots. The appearance of diffraction spots due to the sample entering the X-ray beam is detected, and the position of the sample when the spots first appear is determined. The movement of the sample along the first axis continues until the disappearance of diffraction spots due to the sample exiting the X-ray beam is detected with the sensor, and the position of the sample when the diffraction spots first disappear is determined. These steps are then repeated for the other two sample axes.

Once the foregoing steps are performed for all three of the axes of the coordinate system, six relevant positions have been determined, representing the boundaries of the crystal on two sides in each of the three perpendicular directions. A center of the crystal sample may then be determined by finding the centroid of the six identified coordinates. In one embodiment, the centroid is found by minimizing the sum of the squared Euclidian distances to each of the six points. These steps may also be repeated multiple times as part of an iterative process, and the resulting center determination adjusted to arrive at a more accurate final determination of the crystal sample center.

Detecting the presence of sample spots may be based on different criteria. In one embodiment of the invention, detecting the presence of sample spots comprises detecting a contiguous detector region of at least three pixels with each pixel exceeding a predetermined signal-to-noise ratio, such as two. Determining edge positions from the detector data may also be done in different ways. For example, determining edge positions may include assigning detector readout times to detected diffraction spots and determining an edge position according to the position of the sample at a selected one of said readout times. In one embodiment, by which a "leading" edge may be detected, the selected readout time is the earliest of the assigned readout times. In another embodiment, by which a "trailing" edge may be detected, the selected readout time is the latest of the assigned readout times. The determination of edge positions may also involve extrapolating a readout time from a plurality of diffraction spot data. In such a case, readout times are assigned to detected diffraction spots, and an edge position is determined according to the position of the sample at a readout time that is extrapolated from a gradient of the intensities of the detected diffraction spots relative to readout times.

The method of the exemplary embodiment is particularly useful for single crystal samples. The step of finding an approximate crystal center before beginning the analysis may be done visually, or in any other known manner. Typically, the sample would be mounted in an automated goniometer head (AGH) of the diffractometer, and the AGH would move the sample during the analysis according to a predetermined routine. Different types of active pixel sensors, for example a CMOS-based device, may be used provided they can operate in rolling shutter mode.

DETAILED DESCRIPTION

Figure 1:
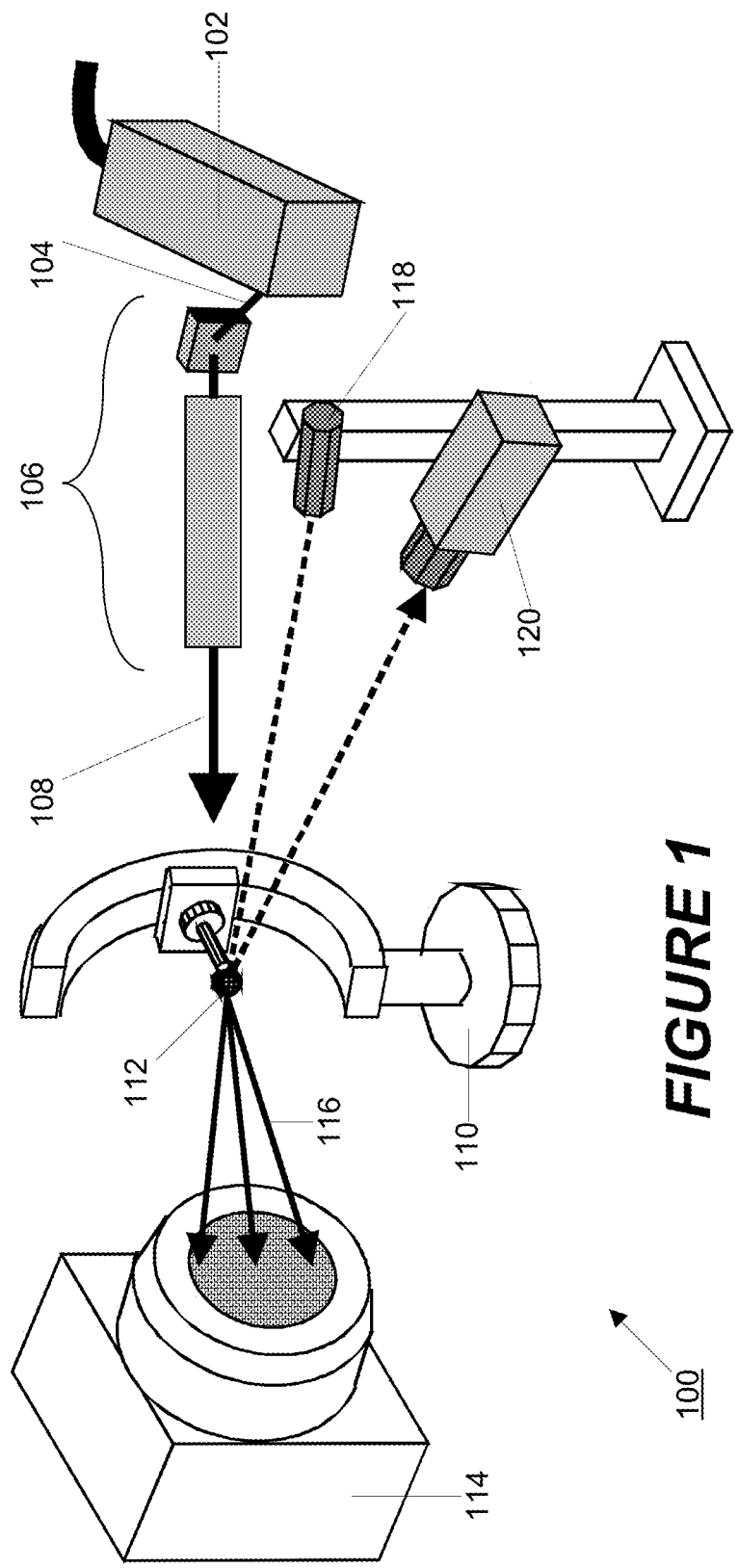
FIG. 1 is a schematic view of a diffractometer configuration that may be used with the present invention.
Figure 2:
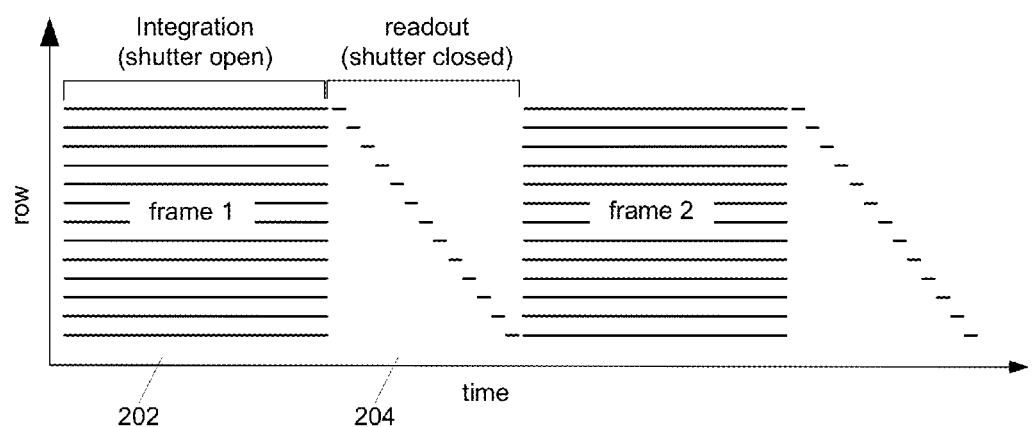
FIG. 2 is a graphical depiction of the conventional frame-by-frame operation of an active pixel sensor.

Shown in FIG. 2 is a schematic depiction of the operation of a pixel array X-ray detector in a conventional readout mode. This detector might be a charge-coupled device (CCD) type detector, such as the APEX II, available from Bruker AXS Inc., Madison, Wis. In this figure, the vertical axis shows the different rows of the two-dimensional detector, and the horizontal axis is indicative of time. The horizontal dimension shows the alternating image collection and readout periods of the detector. As shown, the entire detector surface is active at the same time, as indicated by the "shutter open" label in the figure. Thus, during this integration period 202, all of the detector pixels are active, and are integrating the X-ray energy incident upon them. Each integration period therefore represents one image "frame," and the data collection process continues, collecting additional frames during the subsequent integration periods.

After the collection of each frame of image data, the rows of the detector are read out sequentially by a system controller during the readout period 204. This readout takes a finite amount of time (e.g., 0.5 seconds) during which no further image data is collected. Thus, the pixels of each frame all have the same exposure period, but there is no detection by any of the pixels during the readout period 204. As such, the acquired dataset includes complete images of the entire area of detection, but also has temporal gaps between frames.

In the present invention, centering of the sample is done with the X-ray detector operating in continuous "rolling shutter" mode with an integration time corresponding to the readout time. In the present embodiment, this detector is a complementary metal-oxide-semiconductor (CMOS) type detector which allows active pixel array sensors to have random pixel access capability. A commercial example of such a detector is the PHOTON 100, available from Bruker AXS Inc. The rolling shutter mode of this type of detector is depicted schematically in FIG. 3. In rolling shutter mode, data collection by a particular pixel row of the detector is recommenced immediately after the pixel data for that row is read out. Thus, where the conventional operation shown in FIG. 2 maintains a consistent exposure period across all pixels of the detector, in rolling shutter mode, the temporal exposure period is different for each row of the frame. As such, there is no single frame for which all of the pixels have the same exposure period. However, there is also no significant temporal gap between the frames, as the detection for each row of pixels recommences immediately after that row is read out.

Those skilled in the art will recognize that the constant shifting of the integration period for each consecutive row means that the rows of a given frame are not aligned with each other temporally. However, this is not a problem for the centering routine of the present invention, as it relies not on complete X-ray images of the sample but, rather, on the detection of the edges of the crystal sample during the centering process. This process is discussed in more detail below.

Figure 4:
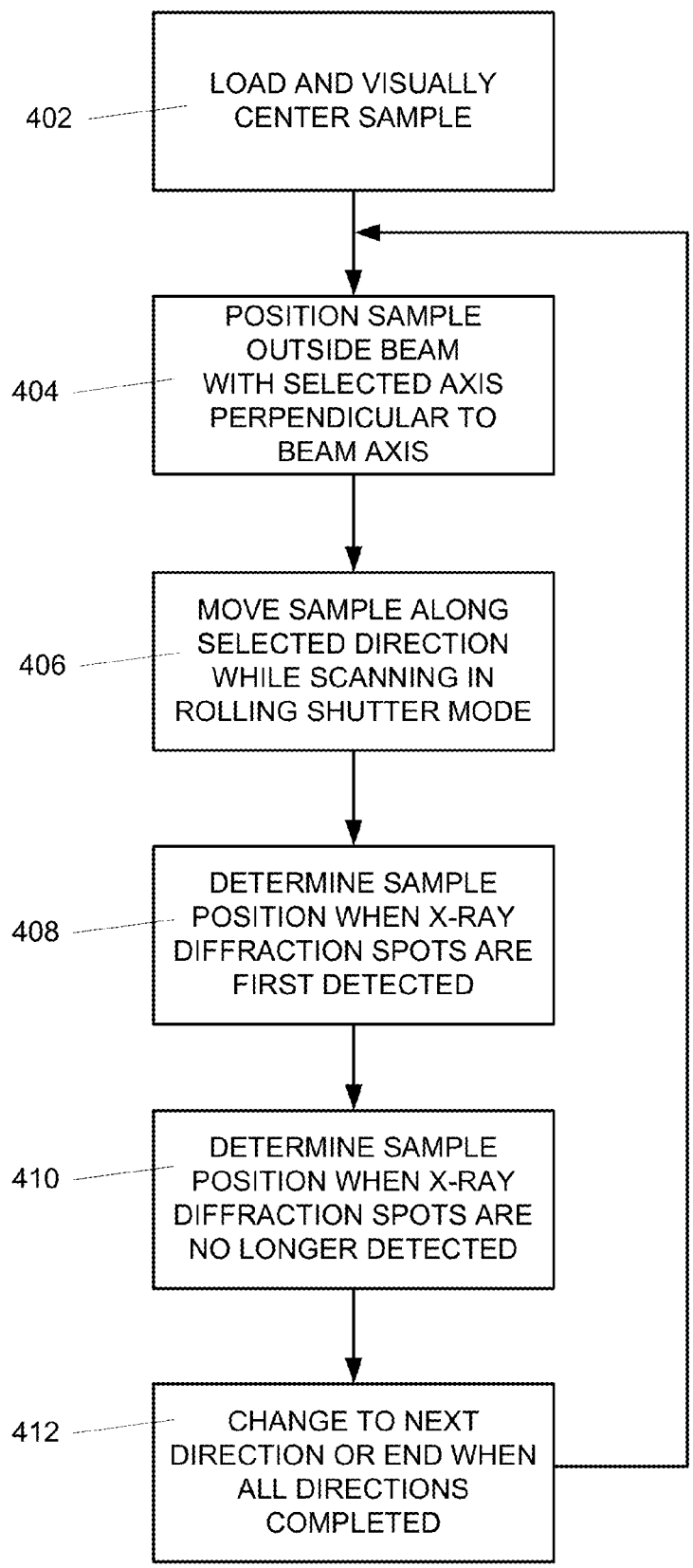
FIG. 4 is a flow diagram showing the steps of an exemplary embodiment of the invention.

FIG. 4 shows a general flow diagram of an exemplary embodiment of the centering method according to the present invention. Using an X-ray detector operated in rolling shutter mode, the sample is positioned in the goniometer using, for example, a conventional sample loop (step 402) and is visually centered. While this visual centering is not highly accurate, it provides a general starting position for the diffraction-based centering method. The approximate center of the sample is also established as the origin of three perpendicular axes passing through the sample. The sample is positioned outside of the X-ray beam such that a selected one of these axes is perpendicular to a central axis of the X-ray beam (step 404). In this embodiment, "outside" the beam is a position at which the crystal sample is not impinged upon by the X-ray beam, and for which there is therefore no X-ray diffraction signal detected. This may be confirmed by verifying that there is no diffraction signal being detected by the X-ray detector, or a location may be simply selected that is far enough from the X-ray beam that there is no possibility of the sample contacting the beam.

Figure 3:
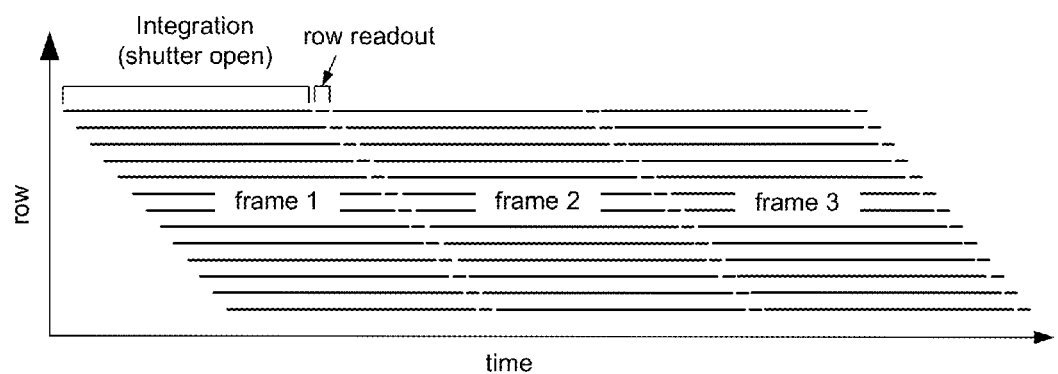
FIG. 3 is a graphical depiction of the rolling shutter operation of an active pixel sensor.

In step 406 of the FIG. 4 method, the sample is moved along the selected axis (e.g., the X-direction) while scanning with the X-ray detector in rolling shutter mode. That is, the X-ray detector is operated as shown in FIG. 3 while the goniometer gradually translates the position of the sample along the chosen direction, while holding it steady in the other two directions. From the data collected, the position of the sample when X-ray diffraction spots are first detected by the X-ray detector is determined (step 408), and this position indicates the location of the first edge of the sample in the direction of movement. Similarly, using the collected data, the position of the sample when X-ray diffraction spots are no longer detected may also be determined (step 410), although the use of this step depends on the specific detection routine being followed, as discussed below. If used, this position indicates the location of the second edge of the sample in that direction and, at this point, the locations of the two edges of the crystal in the chosen direction are known. In step 412 the system then positions the sample for analysis in the next of the three axes (e.g., the Y-direction) and steps 404-410 are repeated for this direction. Finally, the steps of the method are repeated for the third of the perpendicular directions, such that the positions of the crystal edges in all three dimensions are known. Those skilled in the art will recognize that, since this embodiment involves scanning the crystal along three different perpendicular dimensions, it will be necessary to reorient the sample at least one time since, initially, one of the sample axes is parallel to the beam direction.

The data collection in the foregoing example will be continuous as the sample is moved through the beam space, and the determination of the sample position in steps 406 and 408 therefore relies on a correlation between the time at which each row is read out and the location of the sample at that time. Since each row will be read out at a different time, the specific time of readout for the row where diffraction data first appears (or disappears) is used to determine the precise position of the sample at that time. Thus, whether the position determination is done immediately or later as a post-processing step, the correlation between detection and sample position provides an accurate determination of where the edges are located.

With the knowledge of the edges of the crystal sample in three dimensions, the centroid of the six determined coordinates may be found, for example, by minimizing the sum of the squared Euclidian distances to each of the six points, and this point represents the center of the crystal. However, unlike in prior art methods, there are no delays in the capturing of the necessary diffraction data. Since the detector is operating is rolling shutter mode, there is a continuous flow of detector data, albeit row-by-row, that may be relied upon to identify the appearance (and disappearance) of diffraction spots indicative of the presence of the crystal in the X-ray beam. As an overall diffraction image at one point in time is not necessary for the centering routine, there is no detrimental effect of using the rolling shutter mode.

In one embodiment of the invention, the determination of the crystal center involves determining a center point for each of the directions along which the crystal is moved. That is, if the crystal is moved through the first direction, once the two edges in that direction are determined, a center of the crystal along that direction may be determined. This information may also be used to adjust the position of the approximated center of the crystal that represents the origin of the coordinate axes. Thus, if the detection in the first direction reveals a more accurate position of the crystal center in that direction, the presumed origin of the three perpendicular directions may be adjusted accordingly. This process may then be repeated for each of the other two directions as well. Moreover, the detection of all of the crystal edges and the adjustment of the center location may be continually repeated as part of an iterative process that slightly improves the precision of the center determination with each repetition.

Figure 5A:
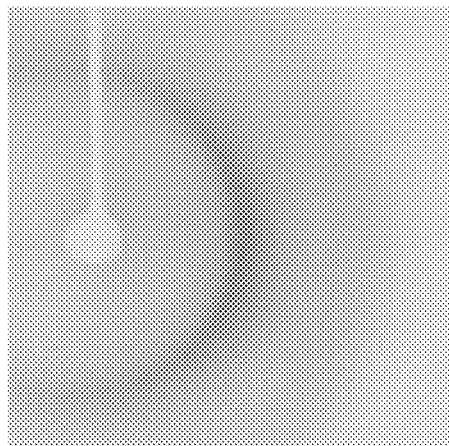
FIGS. 5A-5C show a sequence of images indicating how the presence of diffraction spots may change during a method according to the present invention.
Figure 5B:
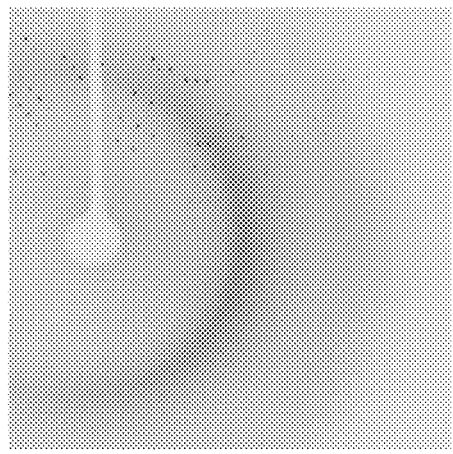
Figure 5C:
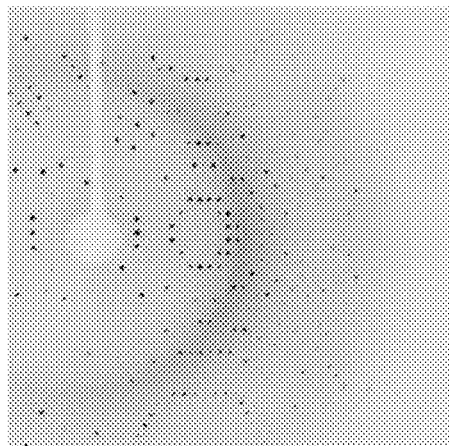

FIGS. 5A-5C show a sequence of images indicative of the detector output in the present invention when the sample moves into the X-ray beam. In FIG. 5A, the sample is outside of the X-ray beam and, as a result, there are no diffraction spots that would be identified by the detector. In FIG. 5B, the translated sample is beginning to enter the beam. The interaction of the crystal sample and the X-ray beam results in diffraction spots being projected across the entire detector surface. However, because the detector is operated in rolling shutter mode, only those spots that are in the region of the detector for which the detector pixels have been read out appear in the accumulated image. In the lower half of the FIG. 5B image, no spots appear, as the pixels corresponding to that region of the detector were read out before the crystal entered the beam. FIG. 5C shows the result when the sample has been in the beam long enough to allow all of the detector pixels to be read out and, as a result, diffraction spots appear throughout the detection frame.

The accuracy of the method will depend on various criteria, including the type of crystal sample and the corresponding number of diffraction spots produced. It will also depend on a desired level of accuracy for the centering method. For example, in the exemplary embodiment, by requiring that 25 diffraction spots within 40 rows of the detector would be necessary to get a detection for a detector having 1024 rows, the resulting accuracy would be approximately 20 ms. In general, the accuracy is limited by the sphere of confusion of the goniometer (about 10 µm in the present example) and the precision of the AGH (about 30 µm in the present example). Using a PHOTON 100 from Bruker AXS (as mentioned above), the AGH can travel about 1 mm in the time that it takes the detector to read out one frame. As such, 1 µm corresponds to about one row, and the 40 µm accuracy corresponds to about 40 rows. Since there are 25*40 rows on the detector, it requires a minimum of 25 diffraction spots equally distributed vertically to match the accuracy.

Because of the manner in which the detector operates in rolling shutter mode, and because the presence of the sample is indicated by a distribution of diffraction spots, the detection of the "leading edge" of the crystal as the sample enters the X-ray beam will be different than the detection of a "trailing edge" as the crystal exits the beam. In some other embodiments, it may be desirable to use just the leading edge detections, and to move the crystal in enough different directions to allow the accurate calculation of a centroid. Several different methods of detecting the crystal edges are discussed below.

Figure 6A:
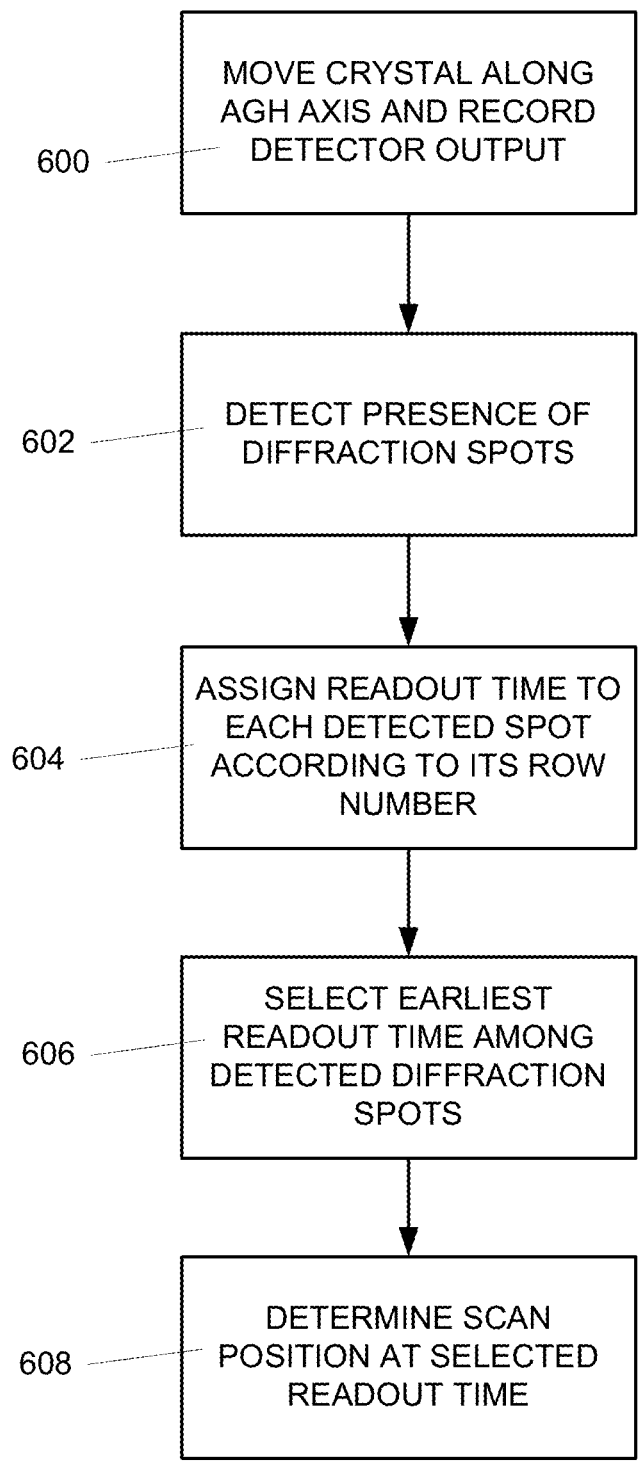
FIG. 6A is a flow diagram showing the steps of a first edge detection method according to the present invention.

A first method is shown in the flow diagram of FIG. 6A, and may be used for determining coordinates corresponding to a leading edge of the sample. In this method, the output of the detector is recorded while the crystal is moved into the X-ray beam in a given direction (step 600). The detection of diffraction spots in this embodiment (step 602) is based on a "blob discovery algorithm." In order to minimize the detection of false positives, a minimum size region of three contiguous pixels is required with each pixel having a minimum signal-to-noise ratio of two, although those skilled in the art will understand that other numbers of pixels or magnitudes may also be chosen. The noise level of a pixel is determined by the Poisson counting statistics of its signal, the read noise characteristics of the active pixel array and the quantization error of the analog-to-digital converter (ADC).

The detector operates in rolling shutter mode, such that a subsequent image frame begins as soon as the previous one ends. It is expected that the initial frames will not contain diffraction spots since the sample has not yet encountered the X-ray beam. However, as detection spots begin to be detected, a readout time is assigned to each spot according to the row number of the detector in which the spot was detected (step 604). The earliest readout time for which a spot is detected is then selected (step 606), and a determination is made as to the scan position at that time (step 608). This position is then used as one of the edge coordinates for determining the center of the sample. As discussed above, the system advances to the next AGH axis when the scan has reached the end of its travel.

Figure 6B:
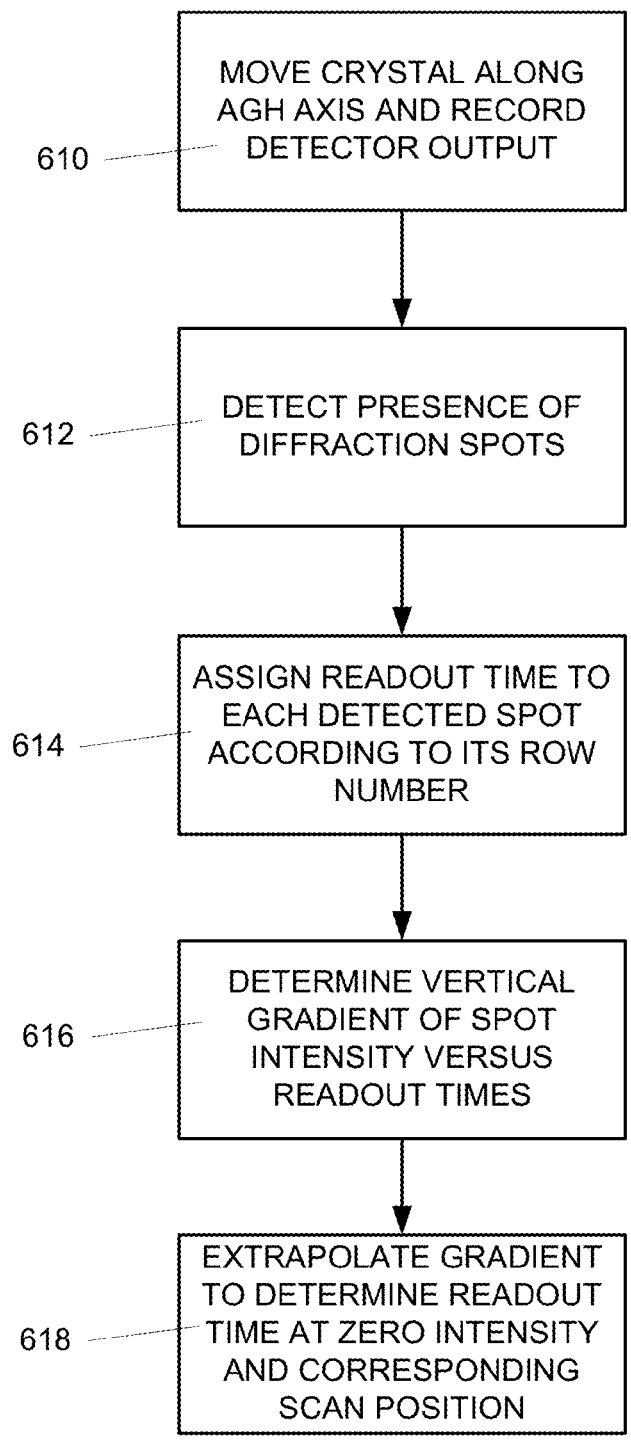
FIG. 6B is a flow diagram showing the steps of a second edge detection method according to the present invention.

Another method for determining coordinates corresponding to a leading edge detection is shown in the flow diagram of FIG. 6B. In this embodiment, the initial steps are the same as those of the embodiment of FIG. 6A, that is, the moving of the crystal and recording of the detector output (step 610), the detection of the presence of diffraction spots (step 612), and the assignment of a readout time to each of the detected diffraction spots (step 614). At this point, however, the detector data are used to calculate a least-squares fit of a vertical linear gradient to the relationship between diffraction spot intensity and assigned readout times (step 616). A straightforward calculation using the diffraction spot intensities provides a gradient that is useful, but somewhat of an approximation, since diffraction spots produced by a crystal typically do not all have the same intensity. A more accurate gradient may be possible by "normalizing" the relative intensities that are detected. For example, the linear gradient may be fitted to the relationship between a ratio $I_t/I_f$ and the assigned readout times, where $I_t$ is the intensity of a diffraction spot in the "transient" image frame (when the crystal is entering or leaving the beam, such as is shown in FIG. 5B), and $I_f$ is the intensity of a diffraction spot in a frame for which the crystal is fully within the beam (such as is shown in FIG. 5C). Whether using the simple gradient or the normalized version, the calculated gradient may then be used to extrapolate a readout time that would correspond to a signal strength of zero and, in the method of FIG. 6B, the scan position at this extrapolated readout time is used as one of the edge coordinates (step 618). Since this is a leading edge detection, the extrapolated readout time may be earlier than those times that correspond to the detection of diffraction spots.

Figure 6C:
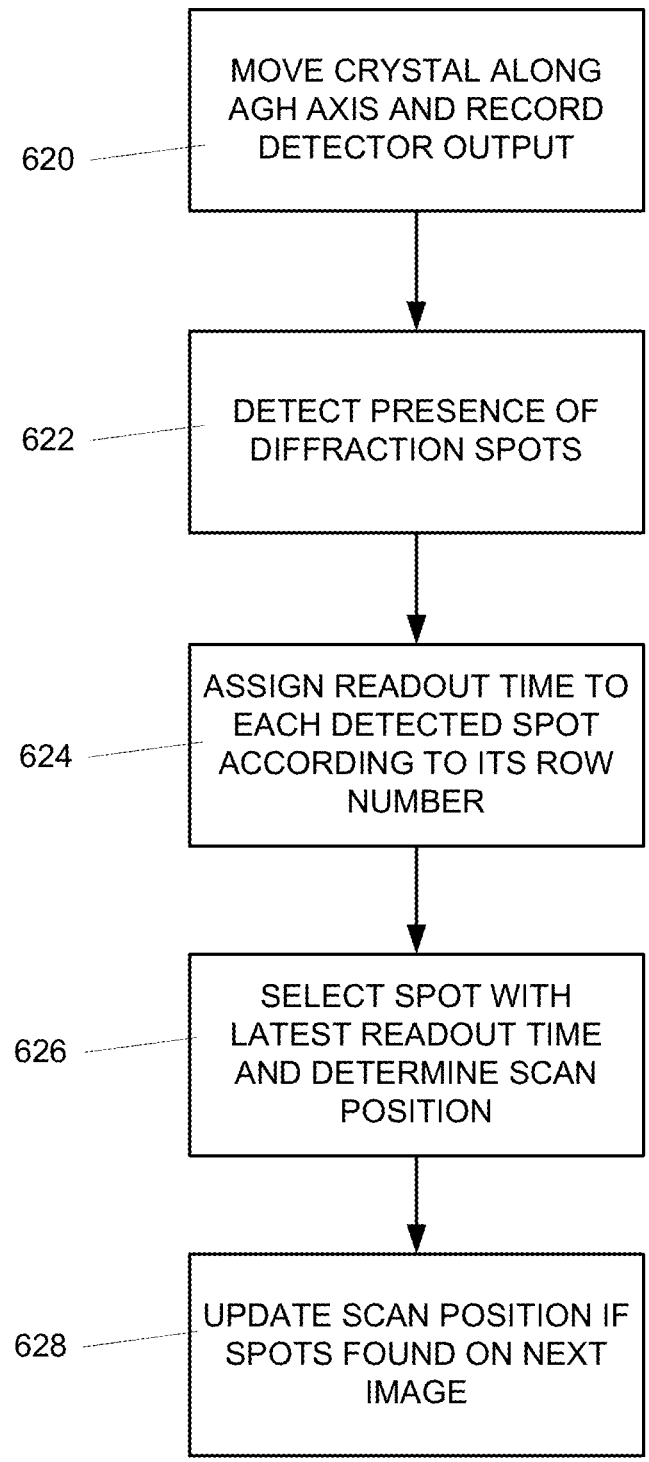
FIG. 6C is a flow diagram showing the steps of a third edge detection method according to the present invention.

The detection of trailing edges is somewhat different than leading edge detection, and a first example is shown by the flow diagram of FIG. 6C. In this method, the first three steps (step 620, step 622 and step 624) are the same as in the methods of FIGS. 6A and 6B. As this method is for the detection of a trailing edge, it is the disappearance of the detected diffraction spots that is relevant. Thus, in step 626, the most recently detected diffraction spot is used to determine a tentative scan position, pending the output of subsequent frames. If detection spots are found on the next image frame, this position value is then updated, being discarded in favor of the position that corresponds to the new "latest" readout time for a detected diffraction spot (step 628). The process continues until a frame with no diffraction spots is encountered. The last selected position is then used as the coordinates for the trailing edge detection. If desired, the scan may be terminated at this point, since the crystal sample has presumably exited the X-ray beam.

Figure 6D:
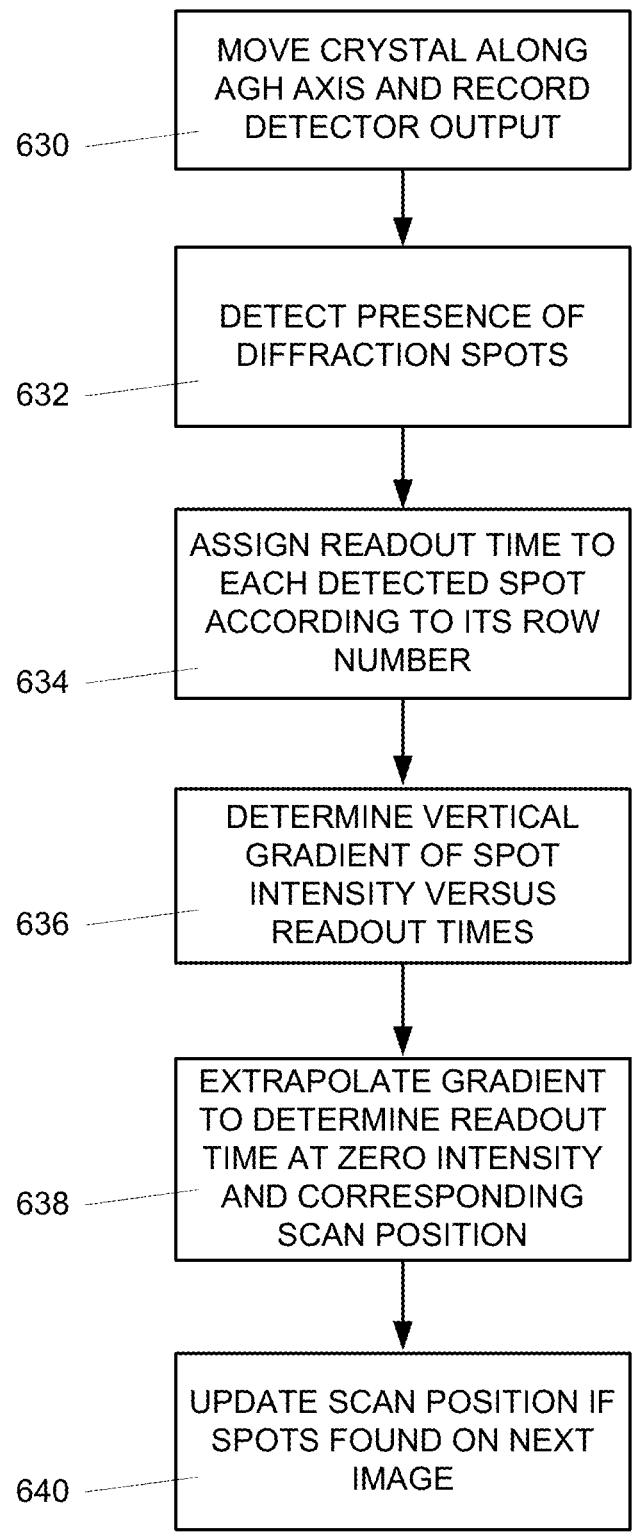
FIG. 6D is a flow diagram showing the steps of a fourth edge detection method according to the present invention.

Another example of a trailing edge detection method is shown in FIG. 6D. Like the leading edge method of FIG. 6B, this version also uses an extrapolation to make a determination of the edge position. The first three steps of this method (steps 630, 632 and 634) are again the same as in those previously described. In step 636, a vertical gradient is determined in the same manner as described above for the embodiment of FIG. 6B, and a readout time is extrapolated that would correspond to a signal strength of zero (step 638). The scan position at this extrapolated readout time may then be selected for use as one of the edge coordinates. While this is similar to the method of the FIG. 6B embodiment, because it is a trailing edge detection the extrapolated readout time may be later than those of actual diffraction spots. Moreover, if there is a detection of any diffraction spots on subsequent images, the selected scan position will be updated to reflect the position corresponding to the newly extrapolated readout time (step 640).

Those skilled in the art will understand that the foregoing details are provided only as examples, and that the specifics of the system will depend on the system components and mode of operation. It will also be understood by those skilled in the art that the invention is not limited to finding crystal edges in three perpendicular directions. More directions may be used, and the directions along which the crystal is moved and/or the crystal position or rotational orientation may be modified during the process. Moreover, as mentioned above, the centering routine may be part of an iterative process during which the position of the presumptive center location is continually updated as additional edge detections are performed.

While the invention has been shown and described with reference to a preferred embodiment thereof, it will be recognized by those skilled in the art that various changes in form and detail may be made herein without departing from the spirit and scope of the invention as defined by the appended claims.

What is claimed is:

1. A method of centering a crystal sample in the X-ray beam of an X-ray diffractometer, the method comprising:
    a) mounting the sample in the diffractometer;
    b) moving the sample in and out of the X-ray beam in a plurality of different directions and detecting the presence of diffraction spots using an active pixel array sensor operating in rolling shutter mode;
    c) determining edge positions of the sample based on sensor readout times that correspond to the appearance and disappearance of detected diffraction spots as the sample is moved; and
    d) using said edge positions to calculate a center of the sample.

2. A method according to claim 1 wherein the detector comprises a CMOS detector.

3. A method according to claim 1 wherein mounting the sample in the diffractometer comprises mounting the sample in an automated goniometer head (AGH) of the diffractometer.

4. A method according to claim 3 wherein moving the sample comprises moving the sample automatically via the AGH.

5. A method according to claim 1 wherein detecting the presence of sample spots comprises detecting a contiguous region of at least three pixels of the active pixel array sensor with each pixel exceeding a predetermined signal-to-noise ratio.

6. A method according to claim 5 wherein said predetermined signal-to-noise ratio equals two.

7. A method according to claim 1 wherein determining edge positions of the sample comprises assigning sensor readout times to detected diffraction spots and determining an edge position according to the position of the sample at a selected one of said readout times.

8. A method according to claim 7 wherein said selected readout time is the earliest of said readout times.

9. A method according to claim 7 wherein said selected readout time is the latest of said readout times.

10. A method according to claim 1 wherein determining edge positions of the sample comprises assigning detector readout times to detected diffraction spots and determining an edge position according to the position of the sample at a readout time that is extrapolated from a gradient of the intensities of detected diffraction spots relative to readout times.

11. A method according to claim 1 wherein using said edge positions to calculate a center of the sample comprises finding a centroid of the determined edge positions.

12. A method according to claim 11 wherein finding said centroid comprises minimizing the sum of the squared Euclidian distances to each of six points representing the determined edge positions.

13. A method according to claim 1 wherein the determining of an approximate center of the sample is done visually.

14. A method of precisely centering a crystal sample in the X-ray beam of an X-ray diffractometer, the method comprising:
   a) mounting the sample in the diffractometer and determining an approximate center of the sample through which three perpendicular sample axes pass;
   b) positioning the sample outside of the X-ray beam such that a first of the sample axes is perpendicular to a center axis of the X-ray beam;
   c) moving the sample toward the X-ray beam along the first axis;
   d) detecting the presence of diffraction spots using an active pixel array sensor operating in rolling shutter mode when the sample enters the X-ray beam, and determining the position of the sample when said diffraction spots first appear;
   e) detecting the absence of diffraction spots using said detector when the sample exits the X-ray beam, and determining the position of the sample when said diffraction spots first disappear; and
   f) repeating steps b) through e) for each of the other two sample axes.

15. A method according to claim 14 further comprising, after step (f):
   g) determining a center of the crystal sample by finding the centroid of six coordinates identified by the respective sample positions determined in steps (d) and (e) for each of the three axes of the coordinate system.

16. A method according to claim 15 further comprising repeating steps (a) through (f) a predetermined number of times and averaging the resulting centroid determinations to arrive at a final determination of said center of the crystal sample.

17. A method according to claim 14 wherein the determining of an approximate center of the sample is done visually.

18. A method according to claim 14 wherein detecting the presence of sample spots comprises detecting a contiguous region of at least three pixels of the active pixel array sensor with each pixel exceeding a predetermined signal-to-noise ratio.

19. A method according to claim 14 wherein determining edge positions of the sample comprises assigning detector readout times to detected diffraction spots and determining an edge position according to the position of the sample at a selected one of said readout times.

20. A method according to claim 14 wherein determining edge positions of the sample comprises assigning detector readout times to detected diffraction spots and determining an edge position according to the position of the sample at a readout time that is extrapolated from a gradient of the intensities of detected diffraction spots relative to readout times.

* * * * *